United States Patent
Jackson et al.

(10) Patent No.: US 6,484,561 B2
(45) Date of Patent: Nov. 26, 2002

(54) EXTERNALLY CRIMPED EXHAUST GAS SENSOR AND METHOD FOR FORMING AN EXTERNAL SHIELD CRIMP

(75) Inventors: Glen Jackson, Henrietta, TX (US); Frank R. Martin, Wichita Falls, TX (US); Jay O'Connell, Sun City Center, FL (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/737,521

(22) Filed: Dec. 15, 2000

(65) Prior Publication Data

US 2002/0100312 A1 Aug. 1, 2002

(51) Int. Cl.[7] ............................................... G01N 27/04
(52) U.S. Cl. ....................................................... 73/31.05
(58) Field of Search ........................... 73/31.05, 31.06, 73/23.31, 23.32; 204/424–429

(56) References Cited

U.S. PATENT DOCUMENTS

| | | | | |
|---|---|---|---|---|
| 4,088,555 A | * | 5/1978 | Kita et al. .................. 204/428 |
| 4,199,425 A | * | 4/1980 | Sinkevitch ................... 204/429 |
| 4,377,801 A | * | 3/1983 | Weber et al. .................. 338/34 |
| 4,842,713 A | * | 6/1989 | Stahl ........................... 204/424 |
| 4,980,044 A | * | 12/1990 | Ker .............................. 204/424 |
| 6,327,891 B1 | * | 12/2001 | Noda et al. .................. 204/424 |

FOREIGN PATENT DOCUMENTS

JP       2306149 A   * 12/1990   ................ 73/31.05

* cited by examiner

Primary Examiner—Daniel S. Larkin
Assistant Examiner—Michael Cygan
(74) Attorney, Agent, or Firm—Vincent A. Cichosz

(57) ABSTRACT

An exhaust gas sensor is made utilizing a crimp wherein an upper shield having a wiring harness assembly and a sub-assembly having a shell are positioned with the optional placement of a lubricant and/or sealant on the shell prior to being joined. Thereafter, the upper shield is crimped over the shell to form the exhaust gas sensor. Thereby, an exhaust gas sensor is made that is free of leaks and resists contamination from water and other contaminants.

9 Claims, 1 Drawing Sheet

EXTERNALLY CRIMPED EXHAUST GAS SENSOR AND METHOD FOR FORMING AN EXTERNAL SHIELD CRIMP

TECHNICAL FIELD

The present invention relates to gas sensors. More particularly, the present invention relates to an externally crimped gas sensor and a method for forming an external shield crimp.

BACKGROUND OF THE INVENTION

Exhaust gas sensors (or exhaust constituent sensors) have been used for many years in automotive vehicles to sense the presence of constituents in exhaust gasses (namely oxygen) and to sense, for example, when an exhaust gas content switches from rich to lean or lean to rich. One known type of exhaust sensor includes a flat plate sensor formed of various layers of ceramic and electrolyte materials laminated and sintered together with electrical circuit and sensor traces placed between the layers in a known manner.

Oxygen sensors are used in the automotive industry to sense amounts of oxygen present in exhaust gases relative to a reference gas, such as air. A switch type oxygen sensor, generally, comprises an ionically conductive solid electrolyte material, a sensing electrode which is exposed to the exhaust gas, and a reference electrode which is exposed to the reference gas. It operates in potentiometric mode, where oxygen partial pressure differences between the exhaust gas and reference gas on opposing faces of the electrochemical cell develop an electromotive force, which can be described by the Nernst equation:

$$E = \left(\frac{RT}{4F}\right)\ln\left(\frac{P_{O_2}^{ref}}{P_{O_2}}\right)$$

where:

E=electromative force
R=universal gas constant
F=Faraday constant
T=absolute temperature of the gas
$P_{O_2}^{ref}$=oxygen partial pressure of the reference gas
$P_{O_2}$=oxygen partial pressure of the exhaust gas The large oxygen partial pressure difference between rich and lean exhaust gas conditions creates a step-like difference in cell output at the stoichiometric point; the switch-like behavior of the sensor enables engine combustion control about stoichiometry. Stoichiometric exhaust gas, which contains unburned hydrocarbons, carbon monoxide, and oxides of nitrogen, can be converted very efficiently to water, carbon dioxide, and nitrogen by automotive three-way catalysts in automotive catalytic converters. In addition to their value for emissions control, the sensors also provide improved fuel economy and drivability.

Because automotive exhaust sensors are mounted to members of the vehicle exhaust flow system, the sensors must be durable, be able to withstand vibration and jarring such as would occur during installation and normal vehicle operation, and be able to withstand shock from the occasional stone or other small road debris that may happen to be thrown at the sensor, for example, by the vehicle's tires.

Typically, great care is required when packaging and holding the flat plate sensing element within the outer housing (body) of the exhaust sensor. The flat plate sensing element can be both difficult and expensive to package within the body of the exhaust sensor since it generally has one dimension that is very thin and is usually made of brittle materials. Consequently, great care and time consuming effort must be taken to prevent the flat plate sensing element from being damaged by exhaust, heat, impact, vibration, the environment, etc. Accordingly, efficient assembly of exhaust sensors such that they are durable and leak free constitutes a substantial concern in the industry.

Protection from contamination and water intrusion into the sensor through all metal/metal interfaces is critical to have long term durability. One such interface is attachment of the external sensor shield, which protects the portion of the exhaust sensor protruding from an exhaust line, to the mounting, or shell, which is threaded to seat the exhaust sensor into a bushing formed in the exhaust line.

Conventional sensors use one of two methods for creating a metal/metal interface between the external sensor shield and the shell. One such method includes welding. However, welding procedures involve significantly high cost processes and complex equipment. Further, production requires long cycle times that are not amenable to low capital investment, lean modules.

A second conventional method involves crimping of the shield inside the shell. The seal provided by this crimp is aided by the reflexive action of the more flexible crimped shield against the inner surface of the more rigid shell. However, labor costs are increased due to process limitations in forming the crimp. Specifically, the process requires that the final exhaust sensor assembly, including the wiring harness be assembled completely on the lower subassembly and that the external sensor shield be crimped after other assembly is completed.

Accordingly, there remains a need in the art for a durable gas sensor having improved resistance to external contaminants and moisture that can be easily manufactured at a low product cost.

SUMMARY OF THE INVENTION

The problems and disadvantages of the prior art are overcome and alleviated by the method for making an exhaust gas sensor. The method comprises positioning a least an end portion of an upper shield having a wiring harness assembly that comprises an upper portion of the sensing element, over at least a first end of a shell whereby the wiring harness assembly and the subassembly converge; and crimping the upper shield end portion over the shell first end.

Further, the gas sensor comprises a sensing element, having an upper portion disposed in electrical communication with a wiring harness assembly and a lower portion disposed within a subassembly; an upper shield disposed around the wiring harness assembly; and a shell disposed around the subassembly, wherein a first end of the shell is concentrically disposed within and crimped to an end portion of the upper shield.

The above-described and other features and advantages of the present invention will be appreciated and understood by those skilled in the art from the following detailed description, drawings, and appended claims.

BRIEF DESCRIPTION OF THE DRAWINGS

The gas sensor and crimping method will now be described by way of example with reference to the following Figure, which is meant to be exemplary, not limiting.

DESCRIPTION OF THE PREFERRED EMBODIMENT

Figure 1:
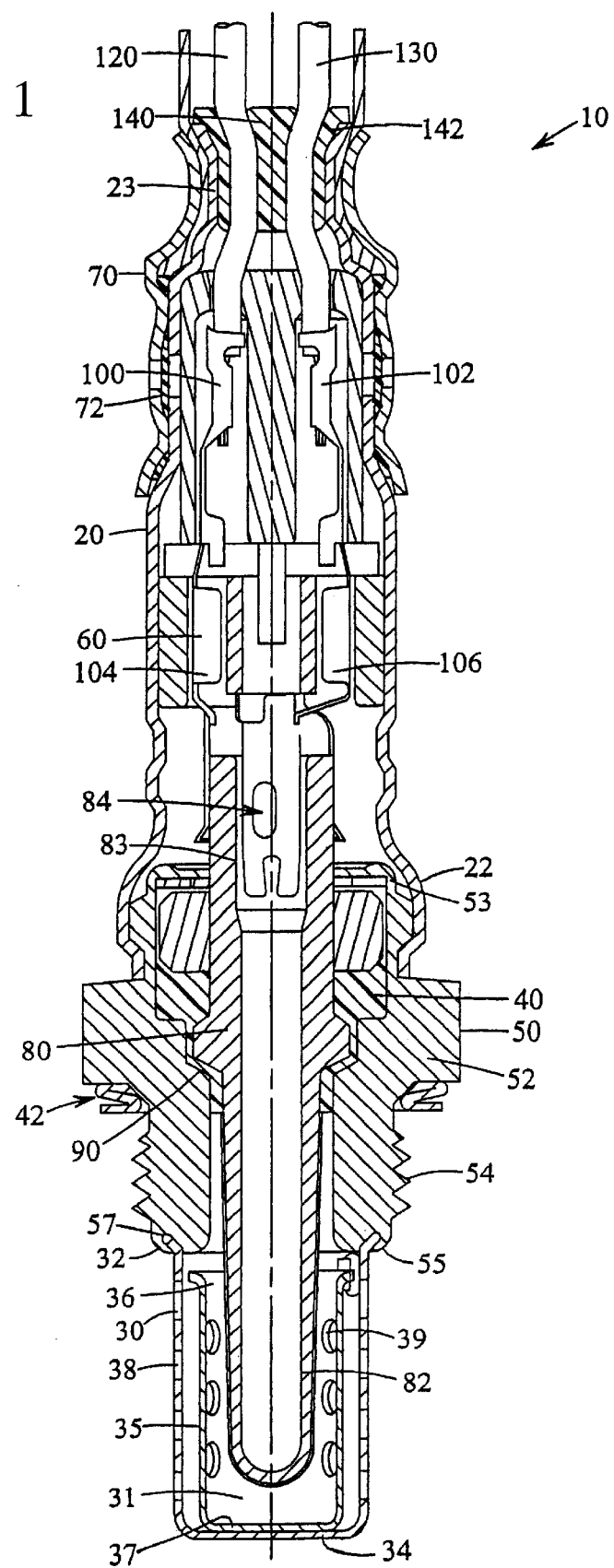
FIG. 1 is a cross-sectional view of an exemplary embodiment of an exhaust sensor using a crimp design.

A gas sensor having an external shield crimp that is free of leaks and a method for making the same is achieved with the use of lubrication, sealant, or a combination comprising at least one of the foregoing. Specifically, the device and processing method allows a protective upper shield, which has a wiring harness assembly, to be converged or attached to a lower exhaust sensor subassembly via an electrical communication with the sensing element. Thereby, preventing water and other contaminants from getting into the sensor through the metal on metal interface of the crimp, and producing a sensor that is generally free of leaks.

Unlike conventional sensors that have the shell crimped over the upper shield, the upper shield herein is first fitted over the shell and is then crimped. This design is contrary to crimping rules of thumb because the shell in this design is inside the upper shield and is also significantly more rigid than the shield being crimped over the shell. Normally, the stiffer member is on the outside of the crimp so that upon relaxation of the material after crimping, force is applied by the inside material. This force is caused by the softer material's greater resiliency to return to its original shape after compression as compared to the harder material.

In contrast, this design functions, in part, because of the combination of the geometries of the crimp groove and the shell and because of the process used to manufacture the sensor. The geometries of the crimp groove and the shell are such that upon crimping the upper shield will fit over the shell. Preferably, the shell has a small portion protruding outward such that the upper shield is crimped beneath the protrusion, e.g., in the crimp groove. The crimp groove should be of appropriate depth to receive the upper shield and securely hold it in place. By crimping the upper shield over the shell, the method of manufacture is more cost effective; such that the wiring harness assembly and the subassembly can be manufactured separately and later assembled.

Referring now to FIG. 1, the example exhaust sensor 10 shown includes a housing structure, a wiring harness and a subassembly. The wiring harness generally includes the electrical components in electrical communication with the upper portion of the sensing element 80 within upper shield 20 and outer shield 70. An upper end 23 of upper shield 20 is disposed beneath outer shield 70. To deter any leakage into or out of sensor 10, a gas leakage inhibitor 72 is disposed between the gap where outer shield 70 overlaps upper shield 20. The typical material for gas leakage inhibitor 72 is a polymeric material, for example, Gore-Tex. The subassembly generally includes the lower portion of the sensing element 80 and an internal shield 35 in lower shield 30 and shell 50. Exemplary materials for the shields 20, 30, 35, and 70 and for the shell 50 are ferrous materials, e.g., stainless steels such as high chrome and/or high nickel stainless steels, and mixtures comprising at least one of the foregoing stainless steels, and the like, with all materials chosen for high temperature endurance, high-strength and corrosion resistance.

Portions of the sensing element 80 are disposed within the upper shield 20, the shell 50 and the lower shield 30. The sensing element 80 can be a planar or flat plate sensing element of a known type. At a first end 82 thereof, disposed in lower shield 30, the sensing element 80 includes a gas constituent-responsive structure fabricated into the sensing element in a known manner, preferably along with a heater of a known type.

To allow an electrical connection of the sensing element 80, a terminal connector 60 is used. The use and type of terminal connecter 60 is known in the art such as an edge card connector or a clam shell connector. Terminal connector 60 may be formed of a thermoplastic or thermoset material (e.g., plastic) or a ceramic durable in the high temperature environments to which the sensor 10 is exposed. Terminal connector 60 typically includes a plurality of electrical terminals with each having a corresponding electrical wire connected thereto. At an opposite end 84 of sensing element 80, lower ends 104 and 106 of terminals 100 and 102, respectively, contact external pads (not shown) on end 84 to provide electrical connection between terminals 100 and 102 and sensing element 80. Ends 104 and 106 of terminals 100 and 102, respectively, are maintained against end 84 of sensing element 80 by a compressive force applied by disposing end 84 of sensing element 80 between lower ends 104 and 106. Preferably, terminals 100 and 102 comprise spring terminals, the use of which is know in the art and the compressive force generated by disposing end 84 between spring terminals 100 and 102 securely maintains end 84 in electrical contact therewith.

For the purpose of illustration only, sensor 10 is shown having a pair of electrical terminals 100 and 102, which are adapted to be connected to electrical wires 120 and 130 in a known manner. Electrical wires 120 and 130 pass through cable seal 140, which generally comprises an elastomeric material suitable for use in a high temperature environment, e.g., spark ignition engine. Cable seal 140 is maintained in place by upper shield 20, which has an upper end 23 forming a seal around a shoulder 142 of cable seal 140, wherein upper shield 20 is crimped in place around cable seal 140 to further secure the same.

Disposed within upper shield 20 and shell 50 is a central portion 83 of sensing element 80, and a high temperature material 90. Optionally, a pair of thermal insulating members (not shown) may be disposed against the sensing element 80 for additional support as is known in the art. The high temperature material 90 is a material that is capable of withstanding the sensor operational conditions and to provide insulation for the sensor 10. Some possible high temperature materials include ceramic fibrous materials, metal mesh, among others, and combinations comprising at least one of the foregoing materials. The ceramic materials can include steatite, alumina, or the like, or combinations comprising at least one of the foregoing materials. When a ceramic fibrous material is used, the orientation and size of the ceramic fibers are not critical to the practice of the present invention. High temperature material 90 may be installed in either a preform or fibrous blanket type state around at least a portion of sensing element 80 as is known in the relevant arts.

Shell 50 includes a body portion 52 and a threaded portion 54 at a second end 55. Body portion 52 is preferably shaped to accommodate a wrench or other tool for tightening threaded portion 54 into a mount for an exhaust pipe or other component of an exhaust flow system, or wherever the gas sensor will be employed, thus enabling a sensor chamber 31 to be located within a flow of gasses to be measured. A first end 53 of shell 50 is disposed proximate and concentrically within lower end 22 of the upper shield 20. Shell 50 is coupled to upper shield 20 by being crimped thereto during the assembly process. To provide additional insulation and vibrational protection, an optional talc pack 40 is disposed within shell 50 adjacent to sensing element 80. Another optional item is gasket 42, which provides a source of tension to help retain sensor 10 in operational position.

In a preferred configuration, lower shield 30 is securely coupled to shell 50 by engaging flared open end 32 of lower shield 30 with annular recess 57 such that a first end 82 of sensing element 80 is disposed within sensing chamber 31 to permit contact with and sensing of exhaust gas. Lower shield 30 defines sensing chamber 31 and, disposed within lower shield 30, is an internal shield 35 which has an open end 36 for receiving sensing element 80 and a closed end 37 adjacent and parallel to closed end 34. Lower shield 30 and internal shield 35 incorporate a plurality of apertures 38, 39 for allowing passage of gas in and out of sensing chamber 31 so that the gasses may be sensed by receptive first end 82 of sensing element 80.

To produce the final assembly, the crimping process generally uses a lubricant and/or a sealant to produce a sensor that is free of leaks. The crimping process generally employs a robust fit of the shield over the shell 50, whereby the upper shield 20 is crimped into the crimp groove below the protrusion of the first end 53. Optionally, the outside of shell 50, corresponding to at least a portion of first end 53, is lubricated prior to or during the insertion process with the upper assembly. Upper shield 20 is then positioned over the shell 50. Thereby, the lubrication facilitates the formation of the leak-free crimp by preventing any significant surface defects from forming along the sidewall of the shell above the crimp. If surface defects were to form along the sidewall of the shell, leak pathways would likely result. An assembly having leak pathways are unacceptable because the device will be susceptible to failure and/or inaccurate readings due to an insufficient resistance to intrusion from water and other contaminants.

Since a heated sensor surface can cause the decomposition of organic lubricants that can contaminate the air reference side of the sensor, cause a depressed voltage reading from the sensor, and results in sub-optimum performance, non-organic lubricants are preferred. The present embodiment prefers alcohol and water solutions since these solutions effectively reduce or prevent scratching of the shell sidewall without organically contaminating the air reference side of the sensor. While any alcohol with sufficient viscosity and volatility can be used, isopropyl alcohol is preferred. Since experimentally, a solution of about 20% alcohol in water solution has promoted excellent lubricating and wetting characteristics, a solution comprising about 15% to about 30% alcohol in water is preferred.

Alternatively, a leak resistant seal can be obtained by employing an inorganic material such as talc, mica, kaolin, and the like, as well as combinations comprising at least one of the foregoing inorganic materials, either alone or with the lubricant. By filling the groove (e.g., at least the portion below the protrusion of first end 53), formed between upper shield 20 and shell 50 with an inorganic material, a reliable seal is created which thereby eliminates the need for welding of the assemblies to form the sensor. The inorganic material flows and packs during crimping and, thereby, eliminates leak paths. This process can be used anywhere a seal is needed and a crimp is used to attach two metallic members in low or high temperatures.

Preferably, talc is employed as the inorganic sealant. The talc sealant allows the sensor to be more tolerant of variations as compared to other sensor formations, such as those using welding. A talc sealant does not prevent surface defects from forming along the sidewall of the shell above the crimp. However, the compressed inorganic sealant flows into the surface defects and forms a watertight seal. Therefore, no appreciable leak paths can be formed through the surface defects because the surface defects are sealed.

In one embodiment of the process, the watertight seal is achieved by dispensing a predetermined amount of a talc and alcohol mixture (e.g. talc and isopropyl alcohol) into the crimp groove of the shell 50 while the subassembly is spinning. This method provides an even distribution of the talc mixture. After spinning, the coated subassembly is dried. Thereafter, the upper shield is fitted onto the shell followed by forming the lower crimp. In forming the lower crimp, the talc captured in the crimp grove is compacted. This compaction provides a watertight seal between the shell and the upper shield. After, the subassembly can optionally be rotated at a controlled speed to dispense an even amount of sealant over the entire circumference of the crimp groove, as preferred.

The sensors made in accordance with the process using inorganic sealant, particularly talc, have a rate of leak that is greatly diminished and, therefore, superior as compared to the rate of leak of competitive parts formed by alternative methods. By having a reduced rate of leakage, these sensors will be less susceptible to problems caused by water and other contaminants that would seep into the internal portions of the sensor.

The sensor preferably comprises an upper shield disposed over and crimped to a shell with an inorganic material disposed there between. This sensor advantageously resists contamination from water and other contaminants by using a crimp of the upper shield and shell of the sensor. Thereby, long-term durability of the sensor is achieved while aiding in the ease of manufacturing.

Furthermore, it is easier to manufacture a sensor by separately building a lower subassembly within the shell and an upper shield that has a wiring harness assembly that are then mated together in a crimping operation. Particularly, this is an improvement over crimps that have the shield inside of the shell. Also, component costs are reduced due to relaxed tolerances of the upper shield and subassembly because a leak-free crimp is formed using the improved method.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A method for making a gas sensor, comprising:

positioning at least an end portion of an upper shield having a wiring harness assembly that comprises an upper portion of the sensing element, over at least a first end of a shell whereby the wiring harness assembly and the subassembly converge; and crimping the upper shield end portion over the shell first end; and disposing a material between at least a portion of the end portion and the first end, wherein the material is selected from the group consisting of lubricants, sealants, and combinations comprising at least one of the foregoing materials.

2. A method for making a gas sensor, comprising positioning at least an end portion of an upper shield having a wiring harness assembly that comprises an upper portion of the sensing element, over at least a first end of a shell whereby the wiring harness assembly and the subassembly converge; and crimping the upper shield end portion over the shell first end;

disposing a material between at least a portion of the end portion and the first end, wherein the material is selected from the group consisting of lubricants, sealants, and combinations comprising at least one of the foregoing materials, wherein the lubricant comprises alcohol.

3. The method of claim 2, wherein the alcohol is isopropyl alcohol.

4. The method of claim 1, wherein the sealant is selected from the group consisting of talc, mica, kaolin, and combinations comprising at least one of the foregoing sealants.

5. The method of claim 4, wherein the sealant is talc.

6. The method of claim 2, wherein the material is a mixture of isopropyl alcohol and talc.

7. A gas sensor, comprising:
a sensing element, having an upper portion disposed in electrical communication with a wiring harness assembly and a lower portion disposed within a subassembly;
an upper shield disposed around the wiring harness assembly;
a shell disposed around the subassembly, wherein a first end of the shell is concentrically disposed within and crimped to an end portion of the upper shield; and
a sealant disposed between at least a portion of the end portion and the first end.

8. The gas sensor of claim 7, wherein the sealant is selected from the group consisting of talc, mica, kaolin, and combinations comprising at least one of the foregoing sealants.

9. The gas sensor of claim 8, wherein the sealant is talc.

* * * * *